United States Patent
Chodorow et al.

[11] Patent Number: 5,290,243
[45] Date of Patent: Mar. 1, 1994

[54] TROCAR SYSTEM

[75] Inventors: Ingram S. Chodorow, Upper Saddle River; M. Zubair Mirza, Wyckoff, both of N.J.

[73] Assignee: Technalytics, Inc., Montvale, N.J.

[21] Appl. No.: 915,337

[22] Filed: Jul. 16, 1992

[51] Int. Cl.$^5$ ............................................. A61M 5/18
[52] U.S. Cl. ................................. 604/165; 606/185
[58] Field of Search ............... 606/182, 185; 604/164, 604/165

[56] References Cited

U.S. PATENT DOCUMENTS 4,931,042  6/1990  Holmes et al. .................. 606/185
5,152,754  10/1992  Plyley et al. .................... 606/185

Primary Examiner—Jerome L. Kruter
Attorney, Agent, or Firm—Curtis Morris & Safford

[57] ABSTRACT

A trocar system is provided for use in obtaining access into a body cavity for laparoscopic/endoscopic procedures. The trocar system includes a protective housing releasably secured to a trocar housing. An obturator shaft is slidably mounted within the housings and has a stylet at an end thereof terminating at a sharp tip. The obturator shaft is movable in a direction of movement between a retracted position, wherein the sharp tip is retracted into the protective housing, and an extended position, wherein the sharp tip extends out of the protective housing. The trocar system also includes a latching and release mechanism provided within the trocar housing for latching the shaft in its extended position and for releasing the shaft to allow retraction thereof to its retracted position. This latching and release mechanism includes a slide plate movable between first and second positions for permitting movement of the obturator shaft between its retracted and extended positions.

46 Claims, 4 Drawing Sheets

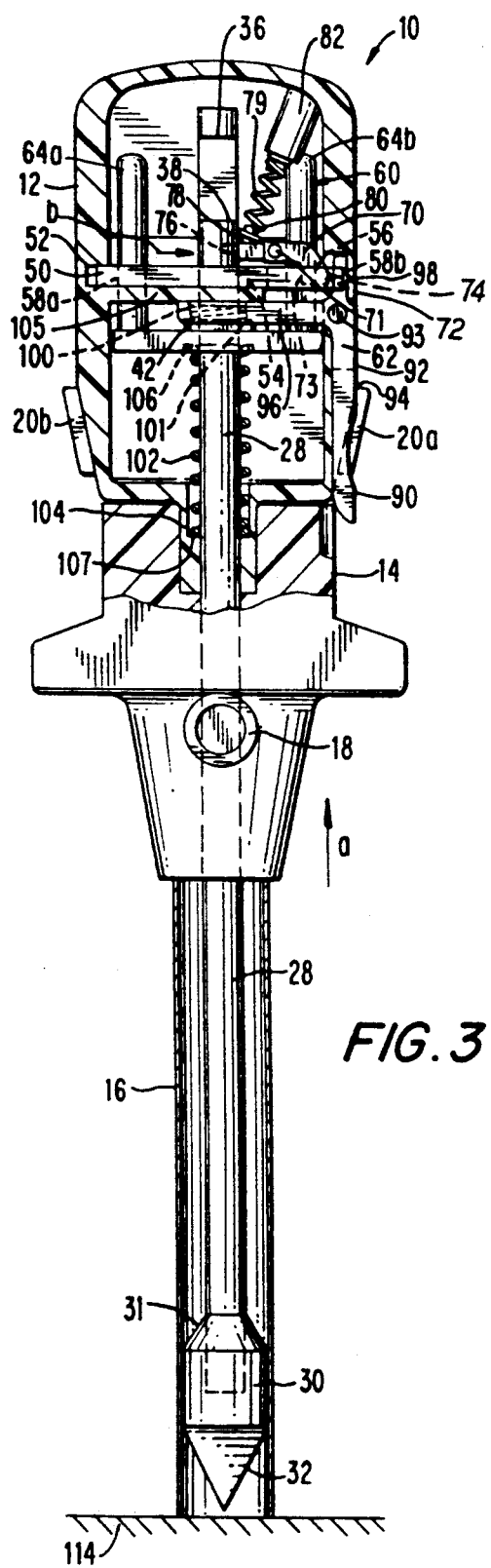
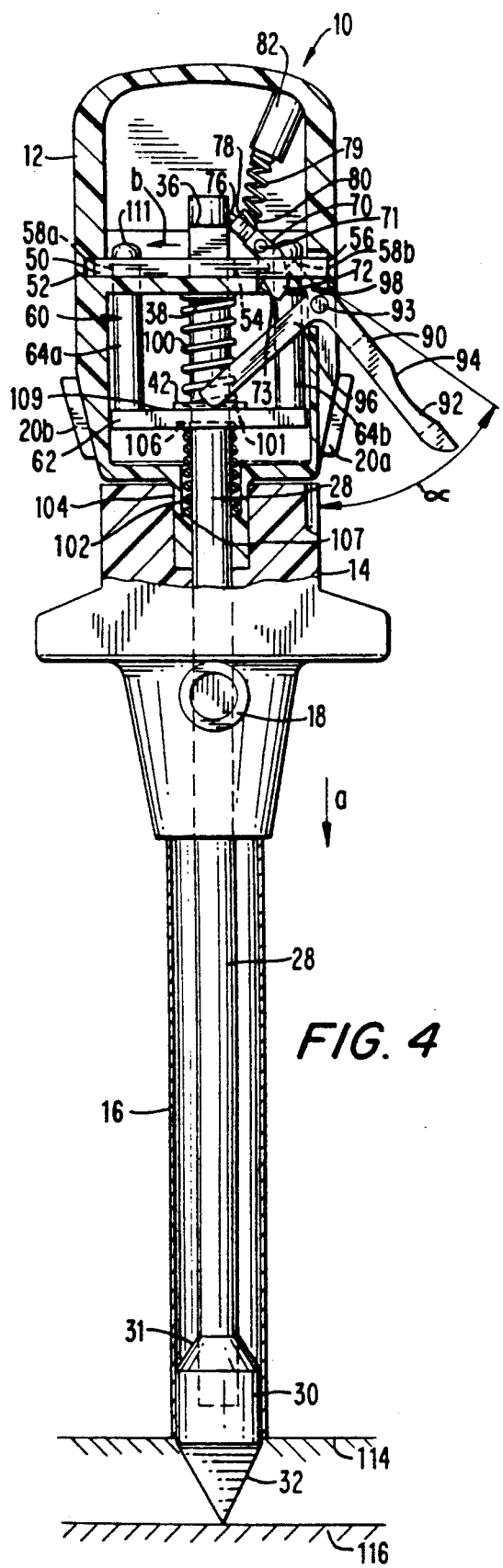
FIG. 3
FIG. 4

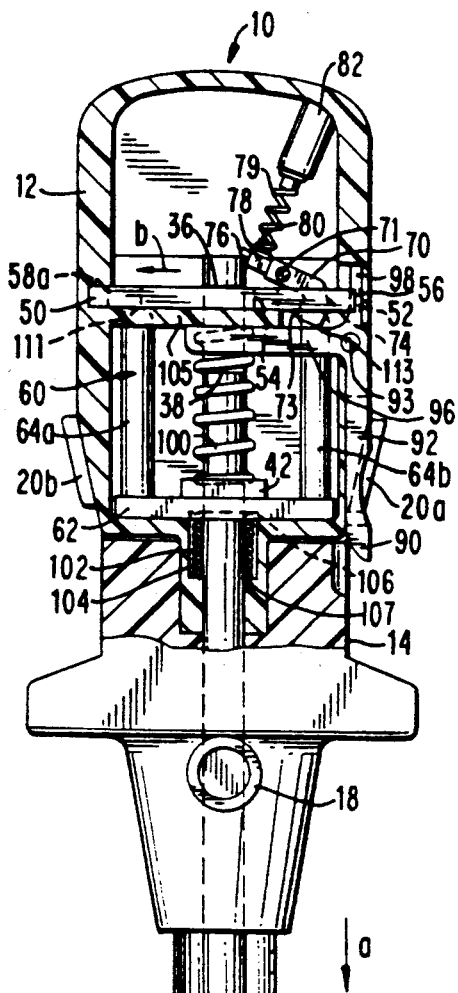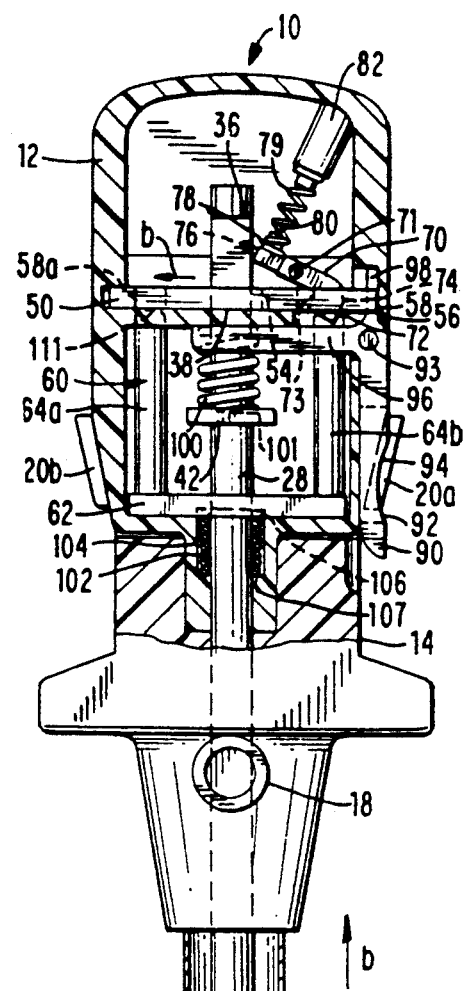
FIG. 5
FIG. 6

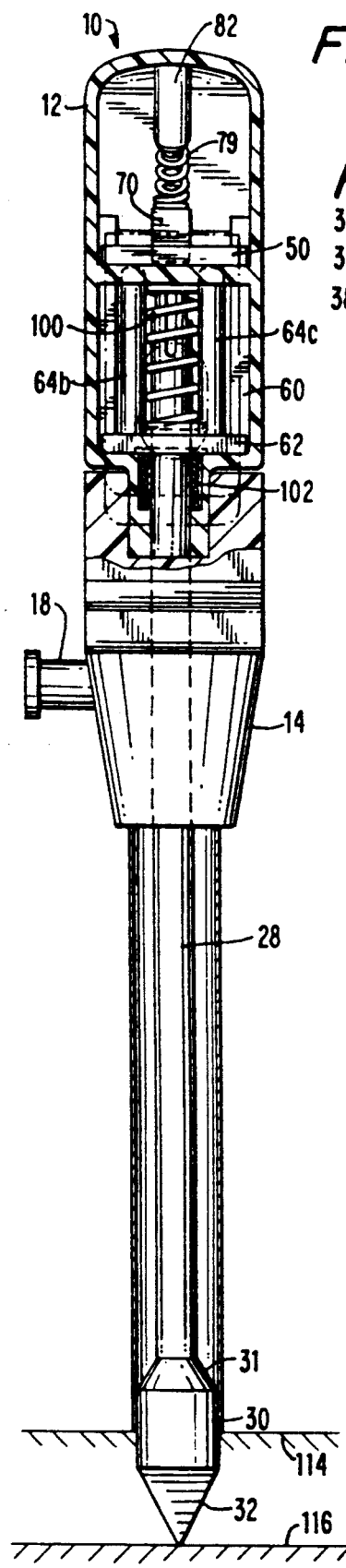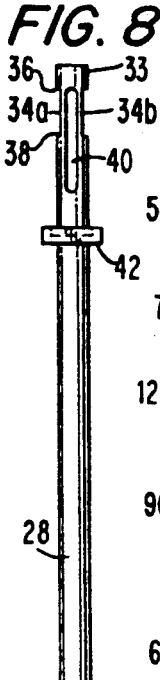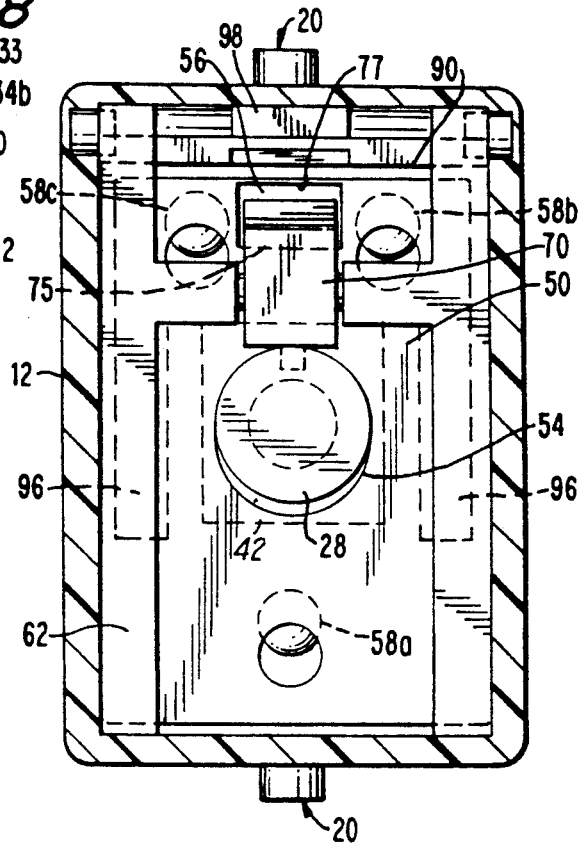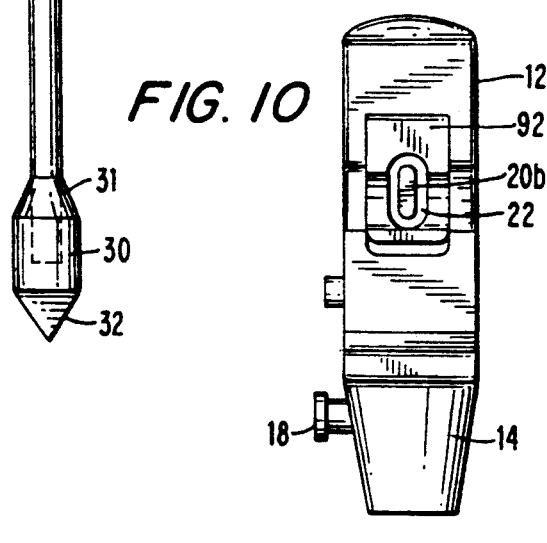

TROCAR SYSTEM

FIELD OF THE INVENTION

This invention relates to a trocar system, and more particularly, to a trocar system in which a sharp cutting tip can be retracted into a protective housing immediately upon entry into the body cavity to prevent inadvertent contact of the sharp tip with a body member.

BACKGROUND OF THE INVENTION

The use of trocars to obtain access into a body cavity for laparoscopic/endoscopic procedures is well known. These types of procedures are currently in use extensively in such procedures as appendectomies, herniorrhaphies, and gall bladder surgery as large incisions in the cavity wall to obtain access to the body member are not necessary.

A trocar generally comprises a trocar housing, a stylet (i.e., a pointed instrument for penetrating a body cavity wall), and a protective housing or cannula surrounding the stylet. The trocar is used to penetrate the body cavity to provide a passageway into the interior thereof such that instruments used during surgery can be extended through the cavity wall to the surgical site. These instruments can include video probes, cutters, surgical staplers, etc.

As a result thereof, in cutting through the body tissue, muscle and membrane of the body cavity wall, resistance to the cutting edge of the trocar is encountered. However, once the tip of the trocar extends through the cavity wall into the body cavity, the resistance to the cutting force of the trocar is significantly reduced. In accordance therewith, trocars in the past have been designed to attempt to obtain a retraction of the sharp tip immediately upon entry of the sharp tip into the body cavity. Without appropriate means to retract the sharp tip, the sharp point could extend further into the body easily injuring a body member. Since the trocar system employs relatively minor incisions in the cavity wall, if a body member is accidentally punctured, the puncture may not become readily apparent until after the laparoscopic/endoscopic procedure. Such a puncturing of the body member will at the very least impede the patient's recovery from the laparoscopic/endoscopic procedure and could mandate corrective surgery.

In the past, prior trocar systems have attempted to provide for retraction of the sharp tip into a protective tube or cannula once the sharp tip enters the body cavity of the patient. For instance, in U.S. Pat. No. 4,902,280 to Lander, a protective tube is positioned over the sharp tip of the stylet to protect the patient from unwarranted cutting, and additionally, the surgeon from injury due to inadvertent contact with the sharp tip. A concentric protective tube is slidably spring-biased in U.S. Pat. No. 4,902,280 to cover the sharp tip of the trocar. In use, the protective tube moves proximally to expose the sharp tip to allow it to puncture the cavity wall. After the sharp tip of the stylet and the protective tube pass fully into the body cavity, the protective tube is able to slide distally under the force of the spring to once again cover the sharp tip of the stylet to prevent inadvertent tissue injury.

U.S. Pat. No. 4,535,773 to Yoon relates to a trocar system wherein the sharp tip of the stylet, which protrudes from a protective housing for the purpose of puncturing tissue, also carries pressure sensors which signal the reduction of pressure due to the sharp tip passing through the cavity wall into the cavity body. This signal causes a solenoid, located within the protective housing, to become energized and thereby disable a detent which retains the stylet in an extended position, thus allowing a pre-tensioned spring to retract the stylet into the protective housing.

The trocar systems of U.S. Pat. Nos. 4,535,773 and 4,902,980, however, have been found to be disadvantageous in implementation. For instance, U.S. Pat. No. 4,902,980 requires that the protective tube in conjunction with the stylet pass fully through the cavity wall in order to invoke its protective features. Thus, the sharp tip does not retract at the moment of peritoneal penetration thus increasing the chance that the sharp tip will extend further through the body cavity puncturing a body member.

A disadvantage of the trocar system disclosed in U.S. Pat. No. 4,902,980 is that since the protective housing surrounding the sharp tip of the stylet penetrates fully through the cavity wall with the stylet into the body cavity, the protective housing can capture body tissue of the cavity wall therein. Obviously, such retainment of tissue can hinder the withdrawal of the protective tube from the cavity wall as the cavity wall trapped by the tube may lead to further complications.

Even though U.S. Pat. No. 4,535,773 teaches a means of retracting the stylet within the housing when the sharp tip enters the body cavity, the impracticality of providing pressure sensors on the stylet and the unreliability of the solenoid together with the need to provide electrical power along with the associate costs of these additional parts combine to make this approach extremely impractical. Additionally, since the necessary sensing equipment for the trocar system of U.S. Pat. No. 4,535,773 is remote from the trocar housing, the retraction of the stylet is delayed thereby reducing the reliability of the trocar system disclosed therein.

OBJECTS OF THE INVENTION

Therefore, it is an object of the present invention to provide a trocar system which avoids the aforementioned disadvantages of the prior art.

An additional object of the present invention is to provide a trocar system incorporating means to immediately and reliably shield the sharp tip of the stylet after the sharp tip has penetrated the body cavity wall.

Another object of the invention is to provide a trocar system which shields the sharp tip of the stylet at all times prior to actual use.

A further object of this invention is to provide for the controlled entry of the sharp tip of the stylet through the cavity wall.

Still another object of this invention is to provide a trocar system wherein the protective housing surrounding the sharp tip of the stylet does not penetrate entirely through the cavity wall with the stylet thus alleviating unwarranted capturing of body tissue within the protective housing upon withdrawal thereof.

An additional object of this invention is to provide a trocar system wherein shielding of the sharp tip of the stylet into the protective housing is accomplished by a simple mechanical apparatus which is reliable and economical to manufacture.

A further object of the present invention is to provide a trocar system incorporating a latching and release mechanism which reliably latches the obturator shaft in its extended position and reliably releases the shaft to allow retraction thereof to its retracted position.

A still further object of the present invention is to provide a trocar system which prevents premature retraction of the obturator shaft when the shaft is in its extended position.

A further object of this invention is to provide a trocar housing which is disposable.

Various other objects, advantages and features of the present invention will become readily apparent from the ensuing detailed description and the novel features will be particularly pointed out in the appended claims.

SUMMARY OF THE INVENTION

In accordance with the present invention, a trocar system is provided for puncturing the body cavity. The trocar includes a trocar housing and a protective housing or cannula releasably attached to the trocar housing. An obturator shaft is slidably mounted within the trocar housing and has a stylet at an end thereof terminating at a sharp tip for cutting the body cavity. The obturator shaft is moveable in a direction of movement between a retracted position, wherein the sharp tip is retracted into the protective housing, and an extended position, wherein the sharp tip extends out of the protective housing for puncturing the body cavity wall.

In accordance with another general object of the present invention, a latching and release mechanism is provided within the trocar housing for reliably latching the shaft in its extended position and for reliably releasing the shaft to allow retraction thereof to its retracted position. In order to permit movement of the obturator shaft between its retracted and extended positions, the latching and release mechanism includes a slide plate moveable between respective first and second positions. The slide plate is reciprocally moveable in the trocar housing in a direction of movement generally normal to the direction of movement of the obturator shaft.

The latching and release mechanism also includes a locking member for releasably locking the slide plate in its first position such that the sharp tip is retracted into the protective housing. The locking member comprises a retraction assembly movable within the trocar housing in a direction of movement of the obturator shaft due to a force applied by the obturator shaft. The retraction assembly includes a generally horizontal platform in biasing contact with the obturator shaft and at least one vertical extension member extending upwardly from the platform which is capable of extending through corresponding openings in the slide plate. The retraction assembly can be moved between an upper position, wherein the vertical extension members extend above the horizontal plane of the slide plate, and lower position, wherein the vertical extension members extend below the corresponding openings of the slide plate such that the slide plate may be slid thereover and moved to its second position such that the sharp tip may be moved to its extended position out of the protective housing to perform its cutting operation.

An assembly is also provided within the latching and release mechanism of the trocar system of the present invention for maintaining the shaft in its retracted position and for providing a reciprocal force to the slide plate. This shaft retention and slide plate moving assembly comprises a spring-biased latch having a cam-shaped surface at one end thereof capable of contacting a latch opening provided in the slide plate, and a pin at the other end thereof which is capable of riding in a keyhole formed in the obturator shaft. This latch is pivotable between a latching position, wherein the pin rides in the keyhole to retain the shaft in its retracted position, and an unlatched position, wherein the cam-shaped surface receives pressure from the slide plate and from the biasing force from a latch spring causing the latch to rotate such that the pin is disengaged from the keyhole thereby permitting movement of the obturator shaft into its extended position.

As an additional safety feature of the present invention, the trocar system herein includes an arming lever for assisting in moving the slide plate into its second position and for assisting in moving the obturator shaft between its retracted and extended positions. The arming lever includes a trigger for pivotally moving the arming lever such that the arming lever contacts both the platform of the retraction assembly and the slide plate. This trigger may be pivotally moved from a rest position, wherein the trigger is closely confined to the trocar housing, to an operating position, wherein the trigger extends outwardly from the trocar housing.

The trigger includes a first arm which protrudes outside of the trocar housing and provides for manual pivotal movement of the arming lever thereby providing for controlled entry of the sharp tip through the cavity wall. In order to provide a direct force on the retraction assembly to move the same between its upper and lower positions, the arming lever also includes a pair of second arms extending generally normal to the trigger and angularly displaceable in the trocar housing so that it is capable of contacting the platform to move the same from its retracted position to its extended position. Simultaneously therewith, a trocar depression spring applies a bearing downward force to a ring member of the shaft to move the shaft into its extended position.

In order to provide the surgeon with the proper line of site during the cutting operation, the trigger does not extend outwardly from the trocar housing after the sharp tip is exposed from the protective housing. Instead, the second arm of the arming lever can be pivotally returned to a reset position by movement of the trigger to its rest position closely confined to the trocar housing without returning the retraction assembly to its upper position or the obturator shaft to its retracted position.

Further, in order to move the slide plate into its second position, the arming lever includes a third arm extending from the trigger which can be pivotally moved by movement of the trigger to contact the slide plate to move the slide plate to its second position. Alternatively, the third arm of the arming lever could also contact the latch such that an abutment portion of the latch contacts an inner edge of the latch opening such that as a result of the force applied thereto, the slide plate is moved to its second position.

As an additional safety feature of the present trocar system, the design of the obturator shaft herein prevents premature retraction thereof when the shaft is in its extended position. In accordance therewith, the shaft includes a shoulder recess formed at the upper end thereof having at least one end flange surface thereof capable of mating engagement with a shaft opening provided in the slide plate to thereby prevent premature retraction of the obturator shaft.

In order to reliably separate the protective housing from the trocar housing, the present invention incorporates a push button release system such that both the trocar housing and protective housing are individually disposable. This separation is provided by push buttons being positioned on both sides of the trocar housing which when depressed separate the protective housing from the trocar housing. In the rest position of the trigger, these push buttons are accessible through a slot formed in the trigger of the arming lever.

BRIEF DESCRIPTION OF THE DRAWINGS

The following detailed description, given by way of example, will best be understood in conjunction with the accompanying drawings in which:

FIG. 3 is a front elevational view of a preferred embodiment of a trocar system in accordance with the present invention illustrating a first retracted position of the obturator shaft.

FIG. 4 is a front elevational view of the trocar system of FIG. 3 illustrating a second partially extended position of the obturator shaft.

FIG. 5 is a front elevational view of the trocar system of FIG. 3 illustrating a third fully extended position of the obturator shaft.

FIG. 6 is a front elevational view of the trocar system of FIG. 3 illustrating a fourth partially retracted position of the obturator shaft.

FIG. 7 is a side elevational view of the trocar system of FIG. 5.

FIG. 8 is a front elevational view of the obturator shaft used in conjunction with the trocar system of FIGS. 3 through 7.

FIG. 9 is a top plan view of the trocar system of FIGS. 3 through 7.

FIG. 10 is a side elevational view of the trocar housing and cannula housing of FIGS. 1 and 2 specifically illustrating a slot in the trigger of the arming lever which exposes a push button release mechanism used to separate the two housings from each other.

DETAILED DESCRIPTION OF A PREFERRED EMBODIMENT

Figure 1:
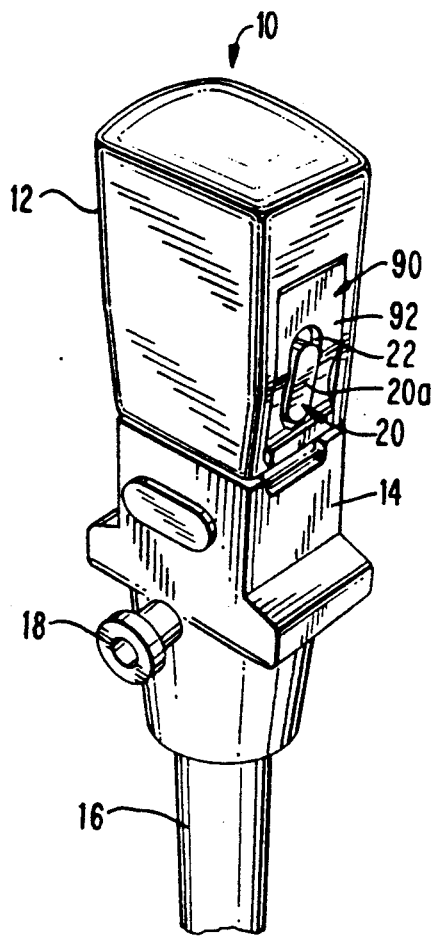
FIGS. 1 and 2 are front perspective views of a preferred embodiment of a cannula housing secured to a trocar housing for a trocar system in accordance with the teachings of the present invention specifically illustrating a trigger of an arming lever being positioned in its rest position and its operating position.

Referring now to the drawings, wherein like reference numerals are used throughout and in particular to FIGS. 1-7, there is illustrated a preferred embodiment of a trocar system in accordance with the present invention. This trocar system is used to obtain access into a body cavity for laparoscopic/endoscopic procedures. As in prior trocar systems, the trocar system of the present invention is used to penetrate the body cavity to provide a passageway into the interior thereof such that instruments used during laparoscopic/endoscopic procedures can be extended through the cavity wall to the surgical site.

Figure 2:
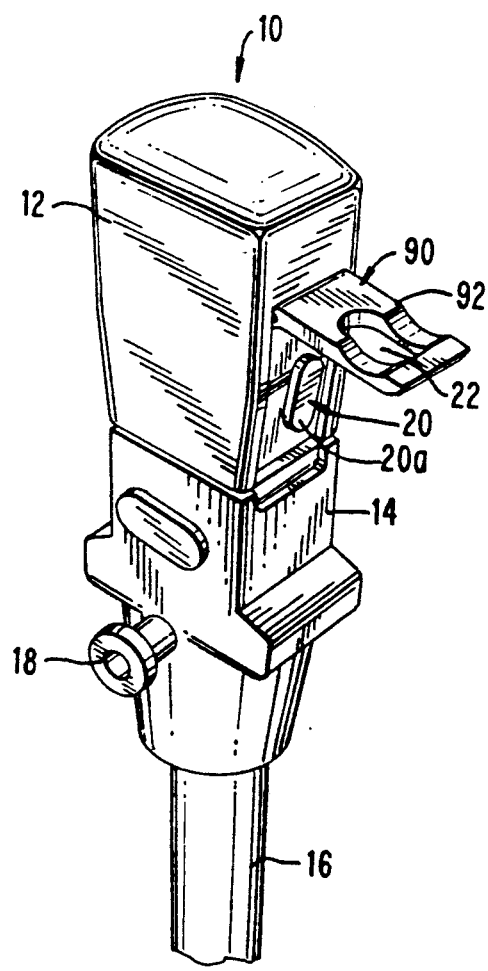

As is shown in FIGS. 1 and 2, the trocar system 10 of the present invention includes a trocar housing 12 enclosing apparatus as will be discussed in more detail below which provides for extension and retraction of an obturator shaft having a sharp tip at an end thereof which is used for cutting the body cavity. A cannula housing 14 and a cannula 16 depending therefrom together form a protective housing which is releasably secured to the trocar housing 12 and protects the sharp tip of the shaft when not performing a cutting operation.

As is shown in FIGS. 1 and 2, a stop-cock valve 18 is provided in the cannula housing 14. When opened, the valve 18 permits the entry of a fluid, such as a gaseous phase carbon dioxide, for insufflation of the body cavity when access thereinto is obtained by use of the trocar system of the present invention.

In order to separate the protective housing, including cannula housing 14 and cannula 16, from trocar housing 12, a push button release mechanism 20 is provided on both sides of trocar housing 12 (see FIGS. 3 through 6). When depressed, the push buttons 20a and b separate the protective housing from the trocar housing. Although not specifically shown in the figures, mechanism used to latch the trocar housing to the protective housing may be in the form of U-shaped leaf spring having outwardly extending latch detents on each end thereof. When the push buttons 20 a and b are depressed, the leaf spring is contracted inwardly thus delatching the trocar housing from the protective housing.

On one side of the trocar housing, push button 20b is accessible through a slot 22 formed in the trigger 92 of an arming lever 90 when the arming lever is in its rest position closely confined to trocar housing 12 (see FIG. 1). When the trigger 92 is moved to its operating position extending outwardly from trocar housing 12, the push button 20b is clearly exposed (see FIG. 2). As a result of this push button release mechanism, the trocar housing and protective housing are individually disposable.

As is shown in FIG. 3, in the trocar system of the present invention, an obturator shaft 28 is slidably mounted within trocar housing 12 and has a stylet 30 at an end 31 thereof terminating at a sharp tip 32 used for cutting the body cavity wall. Thus, in the present trocar system, the obturator shaft 28 and stylet 30 are integrally formed. FIGS. 3-5 illustrate that the obturator shaft 28 is movable in a direction of movement noted by arrow a between a retracted position (see FIG. 3), wherein the sharp tip 32 is retracted into the cannula 16 of the protective housing, and a fully extended position (see FIG. 5), wherein the sharp tip 32 extends outwardly of the cannula 16 for puncturing the body cavity wall.

The structure of obturator shaft 28 is best shown in FIG. 8. At its upper end 33, the obturator shaft 28 includes shoulder recesses 34a and b each having upper and lower end flanged surfaces 36 and 38. A trocar shaft keyhole 40 extends between the shoulder recesses 34a and b. A ring member 42 extends circumferentially around obturator shaft 28 between keyhole 40 and stylet 30 and is formed integrally with shaft 28. As will be discussed in more detail below, force is applied to ring member 42 to move the obturator shaft 28 from its retracted position, as shown in FIG. 3, to its extended position, as shown in FIG. 5.

In accordance with a general object of the present invention, a latching and release mechanism is provided within the trocar housing 12 for reliably latching the shaft 28 in its extended position and for reliably releasing the shaft to allow retraction thereof to its retracted position. As is shown in FIG. 3, the latching and release mechanism includes a slide plate 50, a retraction assembly 60 and a spring-biased latch 70. A brief discussion of each of these components of the trocar system of the present invention follows.

To permit movement of obturator shaft 28 between its retracted and extended positions, slide plate 50 is reciprocally movable within a cavity 52 of trocar housing in a direction of movement, as is designated by arrow b, generally normal to the direction of movement of obturator shaft, as is indicated by arrow a. As will be discussed further, the slide plate is movable within the trocar housing between a first position (as is shown in FIG. 3 with the slide plate 50 slid to the right-hand side of cavity 52), wherein the obturator shaft is retained in its retracted position, and a second position (as is shown in FIG. 5 with the slide plate slid to the left-hand side of cavity 52), wherein the shaft 28 can be moved to its extended position so that the sharp tip 32 is fully extended outwardly of the protective housing.

As is best shown in FIG. 9, the slide plate 50 includes a shaft keyhole 54 through which the obturator shaft 28 vertically extends, a latch keyhole 56 upon which the latch 70 can bear thereagainst, and retractor keyholes, such 58a, b and c, which permit the retractor assembly 60 to move in trocar housing 12 in a predetermined manner in the direction of obturator shaft 28. The shaft keyhole 54 is sized to permit vertical movement of the shaft when the slide plate 50 moves between its first and second positions. However, the retractor keyholes 58a, b, and c are sized to only permit vertical movement of retractor assembly 60 when the slide plate 50 is in its first position.

Retraction assembly 60 defines a locking member for releasably locking slide plate 50 in its first position, as is shown in FIG. 3, such that the sharp tip 32 is retracted into the cannula 16 of the protective housing. The retraction assembly 60 includes a generally horizontal platform 63 in biasing contact with obturator shaft 28 and at least one vertical extension member, such as 64a and 64b, extending upwardly from platform 62. Each of the vertical extension members is capable of extending through one of the respective retractor keyholes, such as 58a and b, when the slide plate 50 is moved to its first position. A third vertical extension member 64c, shown in FIG. 7, is capable of extending through a corresponding retractor keyhole 58c, illustrated in FIG. 9.

As will be discussed in further detail below, upon a downward force being applied to platform 62 by arming lever 90, the retraction assembly 60 is moved between an upper position (see FIG. 3), wherein the vertical extension members 64a and 64b extend above the horizontal plane of slide plate 50 through the respective retractor keyholes 58a and b, and a lower position (see FIG. 5), wherein the upper edge 111 of the vertical extension members 64a and b extends below the horizontal plane of slide plate 50 such that the slide plate may be slid thereover and moved to its second position such that the sharp tip 32 may be moved to its extended position exposed from the cannula 16 to perform its cutting operation.

The spring-biased latch 70 maintains the shaft 28 in its retracted position and provides a reciprocal force to move the slide plate 50 to its second position. The latch 70 has a cam-shaped surface 72 at one end 74 thereof which is capable of bearing against the latch keyhole or opening 56 in the slide plate. An abutment surface 73 is positioned at end 74 opposite to the cam-shaped surface 72. Due to the reciprocal movement of the slide plate, the abutment surface 73 is capable of bearing against an inner edge 75 of latch opening 56 whereas the cam-shaped surface is capable of bearing against an outer edge 77 of latch opening 56 (see FIG. 9).

A pin 76 extends outwardly from latch 70 at the other end 78 thereof and is capable of riding in the shaft keyhole 40 formed in obturator shaft 28. The latch 70 is pivotable about pivot point 71 between a latching position (see FIG. 3), wherein pin 76 rides in the shaft keyhole 40 to retain the shaft in its retracted position, and an unlatched position (see FIG. 5), wherein the cam-shaped surface 72 receives pressure from slide plate 50 and a biasing force from latch spring 79 causing the latch to rotate such that pin 76 is disengaged from trocar shaft keyhole 40 thereby permitting movement of the obturator shaft into its extended position. The latch 70 is thus biased toward its unlatched position by latch spring 79 which extends between an upright member 80 extending generally upwardly from a spring support member 82 extending downwardly from trocar housing 12.

As an additional safety feature of the trocar system of the present invention, an arming lever 90 is provided for assisting in moving slide plate 50 into its second position and for controlling the movement of obturator shaft 28 between its retracted and extended positions, which in turn, provides for controlled entry of the sharp tip through the cavity wall. As is shown in FIG. 3, arming lever 90 includes a trigger 92 for pivotally moving the arming lever about pivot point 93 such that the arming lever contacts both the platform 62 and the slide plate 50. As will be discussed in further detail below, this trigger 92 may be pivotally moved from a rest position (see FIG. 3), wherein the trigger 92 is closely confined to trocar housing 12, to an operating position (see FIG. 4), wherein trigger 92 is pivotally moved about pivot point at an angle $\alpha$ such that it extends outwardly from trocar housing 12.

The trigger 92 is formed of a first arm 94 of the arming lever which protrudes outside of trocar housing 12 and provides for manual controlled movement of arming lever 90 by the surgical team. In order to move the obturator shaft to its extended position, the arming lever also includes a pair of second arms 96 (see FIG. 9) extending generally normal to the trigger first arm 94 and angularly displaceable in the trocar housing so that the second arms 96 are capable of contacting platform 62 and applying a downward force thereto to thereby move the retraction assembly 60 from its upper to its lower position. Simultaneously therewith, a trocar depression spring 100 expands to move the shaft to its extended position as the pin 76 is disengaged from the shaft keyhole 40.

An advantageous feature of the arming lever of the present invention is that the surgeon's line of site is not impeded during the cutting operation as trigger 92 does not extend outwardly from the trocar housing after sharp tip 32 is exposed from the protective housing. Instead, in the fully extended position of sharp tip 32 (see FIG. 5), the trigger 92 may be returned to its rest position closing confined to the trocar housing, which in turn, pivotally returns second arms 96 to a reset position without returning the retraction assembly 60 to its upper position or the obturator shaft 28 to its retracted position as upper end flange surface 36 of shoulder recesses 34a and b engage shaft opening 54 in slide plate 50 to retain the shaft in its extended position.

The arming lever also includes a third arm 98 extending generally upwardly from the trigger 92 in the rest position thereof (see FIG. 3) which can be pivotally moved by movement of the trigger to contact slide plate 50 to move the slide plate to its second position. As a result thereof, the obturator shaft 28 may be moved to its extended position. Alternatively, this third arm 98 of the arming lever could also contact the latch 70 so that the abutment portion 73 of the latch bears against and applies a force to the inner edge 75 of latch opening 56 such that the slide plate may be moved to its second position.

Further, the second arms 96 and third arm 98 are advantageously sized so that the force applied by the third arm 98 to the slide plate 50 is delayed until the vertical extension member, such as 64a, b and c, of the retraction assembly 60 have been pushed below the retractor keyholes, such as 58a, b and c, due to the force applied by second arm 96 to the platform 62.

An assembly is also provided within the trocar housing for biasing said shaft to permit retraction of the shaft immediately upon entry of the sharp tip 32 into the body cavity when no resistance is encountered by the sharp tip, and subsequent thereto, retraction of the retraction assembly 60 to its upward position. This biasing assembly includes the trocar depression spring 100 which is loaded when the shaft 28 is in its retracted position (see FIG. 3), and a retraction spring 102, which is loaded when the retraction assembly 60 is moved to its lower position (see FIG. 5).

Trocar depression spring 100 is seated in a cup-shaped upper surface 101 of ring member 42 of the shaft 28, whereas retraction spring 102 is seated in an annular cavity 104 provided in trocar housing 102. The trocar depression spring 100 is biased between the cup-shaped upper surface 101 of ring member 42 and a horizontal support member 105 extending transversely across trocar housing 12. The retraction spring 102 is biased between a cut-out 106 formed within the bottom surface of platform 62 of retraction assembly 60 and a base surface 107 of annular cavity 104. The retraction spring 102 is loaded when the retraction assembly 60 is moved to its lower position due to a force applied by the second arms 96 of arming lever 90 applying a downward force to platform 62.

FIGS. 3-7 illustrate the normal sequence in utilization of the trocar system 10 of the present invention. FIG. 3 illustrates the shaft 28 in its fully retracted position wherein sharp tip 32 is protected by the cannula 16 of the protective housing. In this retracted position of FIG. 3, the trigger 92 is in its rest position closely confined to the trocar housing 12. The slide plate 50 is positioned within the slide plate cavity 52 in its first position (i.e., toward the right-hand side of cavity 52). The vertical extension members, such as 64a and b, extend above the horizontal plane of slide plate 50 and extend through respective retractor keyholes, such as 58a and 58b, of the slide plate (see FIG. 9). As a result thereof, the slide plate 50 is securely retained in its first position.

As is further shown in FIG. 3, the cam-shaped surface 72 of latch 70 is biased against outer edge 77 of latch opening 56 at one end thereof and pin 76 rides in the shaft keyhole 40 of obturator shaft 28 to thereby retain the shaft in its retracted position. In this retracted position of the shaft, trocar depression spring 100 is loaded between cup-shaped surface 101 of ring member 42 and horizontally extending support member 105. Conversely, the retraction spring 102 is expanded retaining the retraction assembly 60 in its upper position wherein, as discussed above, the vertical extending members, such as 64a and b, extend above the horizontal plane of slide plate 50 through the respective retractor keyholes 58a and b of the slide plate 50.

FIG. 4 illustrates shaft 28 in a partially extended position and illustrates the controlled entry of tip 32 into the cavity wall 114. In this position, the trigger 92 is pivotally moved about pivot point 93 in the manner denoted by angle $\alpha$ such that trigger 92 extends outwardly from trocar housing 12. Upon angularly displaceable movement of trigger 92, second arm 96 contacts platform 62 such that a downward force is applied thereto and the retraction assembly is moved to its lower position. In turn, the trocar depression spring 100 is expanded thereby applying a downward biasing force on ring member 42 to move the shaft to the partially extended position shown in FIG. 4. As a result thereof, the vertical extension members, such as 64a and 64b, of retraction assembly 60 are lowered through respective retractor keyholes 58a and b until the top surface 11 thereof extends below the horizontal plane of slide plate 50 which will be discussed below with reference to the operation step illustrated in FIG. 5. The force applied by second arms 96 to platform 62 also simultaneously contracts retraction spring 102.

FIG. 4 further illustrates that as the trigger 92 is pivotally moved outward from trocar housing 12, the third arm 98 contacts slide plate 50 such that the slide plate is moved to its second position. This permits the obturator shaft 28 to move into its extended position through shaft keyhole 54 of slide plate 50. Since the latch 70 is biased by latch spring 79 towards it unlatched position, when the obturator shaft 28 is moved to its extended position, the latch is pivoted clockwise about pivot point 71 disengaging pin 76 from shaft keyhole 40 of the obturator shaft 28.

Accordingly, as a result of the design of arming lever 90 as is set forth above, the trocar system of the present invention provides for controlled entry of the sharp tip 32 into the body cavity wall. The surgeon can apply a manual force to the trigger 92 sufficient to overcome any resistance encountered by tip 32 to the various layers of the cavity wall 114.

FIGS. 5 and 7 illustrate the fully extended position of sharp tip 32. When the retraction assembly 60 is moved to its lowest position, the upper end 111 of vertical extension members 64a and b extend below the horizontal plane of slide plate 50. With the pin 76 of latch 70 disengaged from shaft keyhole 40, the continued force applied by third arm 98 of arming lever 90 to slide plate 50 in cooperation with the tendency of latch spring 79 to be biased toward the spring unlatched position, the abutment portion 73 of latch 70 contacts inner edge 75 of latch opening 56 to move the slide plate 50 from its first position (as shown in FIGS. 1 and 2) to its second position (i.e., a position within slide plate cavity 52 to the left-hand side thereof). Since the retractor keyholes 58a and b are misaligned with their respective vertical extension members 64a and b, the retraction assembly is retained in its lower position within the trocar housing 12.

As is further shown in FIG. 5, in a fully extended position of obturator shaft 28, the trigger 92 may be returned to its rest position without retracting the obturator shaft as the obturator shaft is retained in its extended position by upper end flanged surface 36 of shoulder recesses 34a and b engaging the shaft keyhole 54 of slide plate 50. Thus, the second arms 96 of the arming lever 90 can be returned to a reset position as is shown in FIG. 5 closely confined to horizontal support member 105.

As aforementioned, the design of the present trocar system advantageously prevents premature retraction of shaft 28 when it is in its extended position as the upper end flanged surface 36 of shoulder recesses 34a and b of shaft 28 matingly engage the shaft opening 54 provided in slide plate 50. Accordingly, a relatively minor decrease in the resistance encountered by sharp tip 32 as it extends through the body cavity wall will not cause the upper end flanged surface 36 to become disengaged from shaft opening 54. In turn, the shaft 28 will not be released from its extended position.

Immediately upon entry of the sharp tip 32 into the body cavity 116, the resistance encountered by the sharp tip dramatically decreases. As a result thereof, the shaft is released from its extended position as the resistance to the cutting operation is insufficient to overcome the biasing force of trocar depression spring 100. Further, as a result thereof, the biasing force of trocar depression spring 100 overcomes the latching force of the upper end flanged surface 36 engaging shaft opening 54. In this situation with the sharp tip encountering virtually no resistance, the trocar depression spring 100 is contracted such that the shaft 28 moves upwardly towards its retracted position, as is shown in FIG. 6. As the shaft 28 is retracted, pin 76 of latch 70 is retained by and engaged within the shaft keyhole 40. Further, the slide plate 50 receives pressure from the cam-shaped surface 72 and, as a result thereof, the slide plate is forced to its first position (see FIG. 3) wherein slide plate 50 is moved to the right-hand side of cavity 52.

As soon as the slide plate is moved to its first position of FIG. 3 and the retractor keyholes, such as 58a and b, are aligned with the upper edge 111 of vertical extension members, such as 64a and b, retraction spring applies a biasing force to the platform 62 such that the retraction assembly 60 is moved upwardly. This causes vertical extension members 64a and b to extend above the horizontal plane of slide plate 50 through the respective retractor keyholes 58a and b and lock the slide plate in its first position as is shown in FIG. 3. The sharp tip is fully retracted into the cannula 16 of the protective housing as is shown in FIG. 3.

It should be understood that the operations described in FIGS. 3-6 are essentially merged and are separated here for ease of discussion.

FIG. 10 further illustrates the push button release mechanism 20 for separating the protective housing (i.e., cannula housing 14 and cannula 16) from trocar housing 12 such that each is individually disposable. As is shown in FIG. 10, the push button 20b is accessible through a slot 22 formed in the trigger 92 of arming lever 90.

Based upon the foregoing, it will be appreciated that a trocar system has been designed which immediately and reliably shields the sharp tip 32 of the stylet 30 of the obturator shaft 28 immediately upon entry of the sharp tip 32 into the body cavity. Further, this trocar system provides for controlled entry of the sharp tip 32 of the stylet through the cavity wall as a result of the design of the arming lever disclosed herein. Further, an advantageous feature of this trocar system is that shielding of the sharp tip 32 of the stylet into the protective housing is accomplished by a simple mechanical apparatus which is reliable and economical to manufacture. Thus, costly sensing equipment to retract the shaft upon entry of the sharp tip into the body cavity is unnecessary. This trocar system of the present invention also advantageously prevents premature retraction of the obturator shaft when the shaft is in its extended position.

While the present invention has been particularly shown and described with reference to a preferred embodiment, it will be readily apparent to those of ordinary skill in the art that various changes and modifications may be made therein without departing from the spirit and scope of the invention. For instance, the retraction assembly may include only the one vertical extension member, such as 64, which includes a stepped section at the upper end thereof which is capable of releasably engaging a retractor keyhole provided in the slide plate. Thus, the slide plate can lock the stepped surface to thereby retain the retractor assembly in its lower position.

It is intended that the appended claims be interpreted as including the foregoing as well as various other such changes and modifications.

What is claimed is:

1. A trocar comprising:
    a trocar housing;
    an obturator shaft slidably mounted within said housing, said obturator shaft having a stylet at an end thereof terminating at a sharp tip, said obturator shaft moveable in a direction of movement between a retracted position and an extended position;
    arming lever means for moving said shaft between its said retracted and extended positions, wherein said arming lever means includes trigger means for pivotally moving said arming lever means such that said arming lever means permits said shaft to move the same between its said retracted and extended positions;
    biasing means provided within said trocar housing for biasing said shaft; and
    latching and release means provided within said trocar housing for latching said shaft in its said extended position and for releasing said shaft to allow retraction thereof to said retracted position.

2. The trocar of claim 1 wherein said trigger means includes first arm means protruding outside said trocar housing for manual pivotal movement of said arming lever means.

3. The trocar of claim 2 wherein said means for permitting said obturator shaft to move between said retracted and extended positions includes second arm means of said arming lever means extending generally normal to said trigger means and angularly displaceable in said trocar housing and capable of cooperatively permitting movement of said obturator shaft from its said retracted position to its said extended position.

4. A trocar comprising:
    a trocar housing;
    an obturator shaft slidably mounted within said housing, said obturator shaft having a stylet at an end thereof terminating at a sharp tip, said obturator shaft moveable in a direction of movement between a retracted position and an extended position;
    biasing means provided within said trocar housing for biasing said shaft;
    latching and release means provided within said trocar housing for latching said shaft in its said extended position and for releasing said shaft to allow retraction thereof to said retracted position, wherein said latching and release means includes slide plate means moveable between first and second positions for permitting movement of said obturator shaft between said retracted and extended positions; and arming lever means providing means for moving said slide plate means into said second position.

5. The trocar of claim 4 wherein said latching and release means includes shaft retention means and plate moving means for maintaining said shaft in its said retracted position and for providing a reciprocal force to said slide plate means.

6. The trocar of claim 5 wherein said retention means includes a spring-biased latch having a cam-shaped surface capable of contacting a latch opening of said slide plate means at one end thereof.

7. The trocar of claim 6 wherein said means for moving said slide plate means into its said second position includes a generally upwardly extending member of said arming lever means which can be pivotally moved to contact said slide plate means to move said slide plate means to its said second position.

8. The trocar of claim 7 wherein said generally vertically upwardly member can contact said latch such that an abutment portion of said latch contacts an inner edge of said latch opening such that as a result of the force applied thereto said slide plate means is moved to its said second position.

9. The trocar of claim 8 wherein said abutment portion and said cam-shaped surface are formed on opposite sides of a downwardly depending member of said latch which extends into said latch opening of said slide plate means.

10. A trocar comprising;
a trocar housing;
a protective housing releasably attached to said trocar housing;
an obturator shaft slidably mounted within said housing, said obturator shaft having a stylet at an end thereof terminating at a sharp tip, said obturator shaft moveable in a direction of movement between a retracted position, wherein said sharp tip is retracted into said protective housing, and an extended position, wherein said sharp tip extends out of said protective housing; and
arming lever means for moving said shaft between its said retracted and extended positions, wherein said arming lever means includes trigger means for pivotally moving said arming lever means such that said shaft can move between its said retracted and extended positions; and
latching and release means provided within said trocar housing for latching said shaft in its said extended position and for releasing said shaft to allow retraction thereof to said retracted position.

11. The trocar of claim 10 wherein said trigger means may be pivotally moved from a rest position, wherein said trigger means is closely confined to said trocar housing, to an operating position, wherein said trigger means extends outwardly from said trocar housing.

12. The trocar of claim 11 and further including push button release means for separating said protective housing from said trocar housing.

13. The trocar of claim 12 wherein said push button release means comprise a push button being provided on both sides of said trocar housing which when depressed separate said protective housing from said trocar housing.

14. The trocar of claim 13 wherein in said rest position of said trigger means, said push button is accessible through a slot formed in said trigger means 15. A trocar comprising;
a trocar housing;
a protective housing releasably attached to said trocar housing;
an obturator shaft slidably mounted within said housing, said obturator shaft having a stylet at an end thereof terminating at a sharp tip, said obturator shaft moveable in a direction of movement between a retracted position, wherein said sharp tip is retracted into said protective housing, and an extended position, wherein said sharp tip extends out of said protective housing;
arming lever means for moving said shaft between its said retracted and extended positions, wherein said arming lever means includes trigger means for moving said arming lever means; and
push button release means for separating said protective housing from said trocar housing which is accessible through a slot formed in said trigger means when said trigger means is closely confined to said trocar housing.

16. A trocar comprising:
a trocar housing;
an obturator shaft slidably mounted within said housing, said obturator shaft having a stylet at an end thereof terminating at a sharp tip, said obturator shaft moveable in a direction of movement between a retracted position and an and an extended position;
biasing means provided within said trocar housing for biasing said shaft; and
latching and release means provided within said trocar housing for latching said shaft in its said extended position and for releasing said shaft to allow retraction thereof to said retracted position, wherein said latching and release means includes slide plate means moveable between first and second positions for permitting movement of said obturator shaft between said retracted and extended positions, said latching and release means further including locking means for releasably locking said slide plate means in its said first position, said locking means including a retraction assembly movable within said trocar housing in the direction of movement of said obturator shaft, and said retraction assembly including a generally horizontal platform in biasing contact with said obturator shaft and at least one vertical extension member extending upwardly from said platform capable of extending through corresponding openings in said slide plate means.

17. The trocar of claim 16 wherein said retraction assembly is moveable between an upper position, wherein said vertical extension members extend above the horizontal plane of said slide plate means, and a lower position, wherein said vertical extension members extend below said corresponding openings of said slide plate means such that said slide plate means may be slid thereover and moved to its said second position.

18. The trocar of claim 17 wherein said biasing means includes a trocar depression spring which is loaded when said shaft is in its retracted position, and a retraction spring, which is loaded when said retraction assembly is moved to its said lower position.

19. The trocar of claim 18 wherein said trocar depression spring is seated in a cup-shaped upper surface of said ring member.

20. The trocar of claim 19 wherein said retraction spring is seated in an annular cavity of said trocar housing and loaded due to a force applied by said platform when said retraction assembly is moved to its said lower position.

21. The trocar of claim 20 wherein said shaft is released from its said extended position when the biasing force of said depression spring overcomes the resistance force encountered by said sharp tip.

22. The trocar of claims 17 wherein said latching and release means further includes shaft retention and plate moving means for maintaining said shaft in its said retracted position and for providing a reciprocal force to said slide plate means.

23. The trocar of claim 22 wherein said shaft retention and plate moving means includes a spring-biased latch having a cam-shaped surface at one end thereof capable of contacting a latch opening of said slide plate means and a pin at the other end thereof which is capable of riding in a keyhole formed in said obturator shaft.

24. The trocar of claim 23 wherein said latch is pivotable between a latching position, wherein said pin rides in said keyhole to retain said shaft in its retracted position, and an unlatched position, wherein said cam-shaped surface receives pressure from said slide plate means causing said latch to rotate such that said pin is disengaged from said keyhole thereby permitting movement of said obturator shaft to its said extended position.

25. The trocar of claim 24 wherein said latch is biased toward said unlatched position.

26. The trocar of claim 23 and further including arming lever means providing means for moving said slide plate means into its said second position and means for cooperatively moving said retraction assembly from its said upper position to said lower position.

27. The trocar of claim 26 wherein said arming lever means includes trigger means for pivotally moving said arming lever means such that said arming lever means contacts said retraction assembly and said slide plate means.

28. The trocar of claim 27 wherein said trigger means includes first arm means protruding outside said trocar housing for manual pivotal movement of said arming lever means.

29. The trocar of claim 27 wherein said means for moving said retraction assembly between said retracted and extended positions includes second arm means of said arming lever means extending generally normal to said trigger means and angularly displaceable in said trocar housing and capable of contacting said retraction assembly to move said retraction assembly from its said retracted position to its said extended position and permit said obturator shaft to move from its retracted position to its extended position.

30. The trocar of claim 29 wherein said second arm means can be pivotally returned to a reset position by movement of said trigger means without returning said obturator shaft to its said retracted position.

31. The trocar of claim 30 wherein in said reset position, said trigger means is closely confined to said trocar housing to enhance the surgical line of site during a cutting operation.

32. The trocar of claim 27 wherein said means for moving said slide plate means into its said second position includes third arm means of said arming lever means extending from said trigger means which can be pivotally moved by movement of said trigger means to contact said slide plate means to move said slide plate means to its said second position.

33. The trocar of claim 32 wherein said third arm means can contact said latch such that an abutment portion of said latch contacts an inner edge of said latch opening such that as a result of the force applied thereto said slide plate means is moved to its said second position.

34. The trocar of claim 33 wherein said abutment portion and said cam-shaped surface are on opposite sides of a downwardly depending member of said latch which extends into said latch opening of said slide plate means.

35. A trocar comprising:
a trocar housing;
an obturator shaft slidably mounted within said housing, said obturator shaft having a stylet at an end thereof terminating at a sharp tip, said obturator shaft moveable in a direction of movement between a retracted position and an extended position;
biasing means provided within said trocar housing for biasing said shaft; and
latching and release means provided within said trocar housing for latching said shaft in its said extended position and for releasing said shaft to allow retraction thereof to said retracted position, wherein said latching and release means includes slide plate means moveable between first and second positions for permitting movement of said obturator shaft between said retracted and extended positions, wherein said obturator shaft includes means for preventing premature retraction thereof when said shaft is in its said extended position which comprise a shoulder recess formed at the upper end of said obturator shaft having at least one end thereof capable of mating engagement with a shaft opening of said slide plate means to thereby prevent premature retraction of said obturator shaft.

36. A trocar comprising:
a trocar housing;
an obturator shaft slidably mounted within said housing, said obturator shaft having a stylet at an end thereof terminating at a sharp tip, said obturator shaft moveable in a direction of movement between a retracted position and an extended position; and
latching and release means provided within said trocar housing for latching said shaft in its said extended position and for releasing said shaft to allow retraction thereof to said retracted position, wherein said latching and release means further includes retention means for maintaining said shaft in its said retracted position, said retention means including a spring-biased latch having a pin at one end thereof which is capable of riding in a keyhole formed in said obturator shaft to retain said shaft in its retracted position, said latching and release means further including slide plate means movable between first and second positions for permitting movement of said obturator shaft between said retracted and extended positions, and wherein said spring-biased latch further includes a cam-shaped surface at another end thereof capable of contacting a latch opening of said slide plate means.

37. The trocar of claim 36 wherein said latch is pivotable between a latching position, wherein said pin rides in said keyhole to retain said shaft in its said retracted position, and an unlatched position, wherein said cam-shaped surface receives pressure from said slide plate means causing said latch to rotate such that said pin is disengaged from said keyhole thereby permitting movement of said obturator shaft to its said extended position.

38. The trocar of claim 37 wherein said latch is biased toward said unlatched position.

39. A trocar comprising:
a trocar housing;
an obturator shaft slidably mounted within said housing, said obturator shaft having a stylet at an end thereof terminating at a sharp tip, said obturator shaft moveable in a direction of movement between a retracted position and an extended position;
biasing means provided within said trocar housing for biasing said shaft; and
latching and release means provided within said trocar housing for latching said shaft in its said extended position and for releasing said shaft to allow retraction thereof to said retracted position, wherein said latching and release means includes locking means for permitting movement of said obturator shaft from its said retracted position to its said extended position, said locking means including a retraction assembly moveable within said trocar housing in the direction of movement of said obturator shaft and is moveable between upper and lower positions within said trocar housing, said retraction assembly including a generally horizontal platform in biasing contact with said obturator shaft and at least one vertical extension member extending upwardly from said platform, said latching and release means further including slide plate means moveable between first and second positions for permitting movement of said obturator shaft between said extended and retracted positions, and wherein in said upper position of said retraction member, said at least one vertical extension member extends above the horizontal plane of said slide plate means, and in said lower position of said retraction assembly, said at least one vertical extension member extends below corresponding retraction assembly keyholes of said slide plate means such that said slide plate means can be slide thereover and moved into its said second position.

40. The trocar of claim 39 wherein said biasing means includes a trocar depression spring biased towards said extended position of said shaft and loaded when said shaft is in its retracted position, and a retraction spring biased towards said retracted position of said shaft and loaded when said retraction assembly is moved to its said lower position.

41. The trocar of claim 40 wherein said trocar depression spring is seated in a cup-shaped upper surface of said ring member.

42. The trocar of claim 41 wherein said retraction spring is seated in an annular cavity of said trocar housing and loaded due to a force applied by said platform when said retraction assembly is moved to its said lower position.

43. The trocar of claim 42 wherein said shaft is released from its said extended position when the biasing force of said depression spring overcomes the resistance force encountered by said sharp tip.

44. A trocar comprising:
a trocar housing;
an obturator shaft slidably mounted within said housing, said obturator shaft having a stylet at an end thereof terminating at a sharp tip, said obturator shaft moveable in a direction of movement between a retracted position and an extended position;
biasing means provided within said trocar housing for biasing said shaft, said biasing means including a trocar depression spring biased towards said extended position of said shaft and a retraction spring biased toward said retracted position of said shaft; and
latching and release means provided within said trocar housing for latching said shaft in its said extended position and for releasing said shaft to allow retraction thereof to said retracted position, wherein said shaft is released from its said extended position when the biasing force of said depression spring overcomes the resistance force encountered by said sharp tip.

45. The trocar of claim 44 wherein said latching and release means includes a retraction assembly moveable within said trocar housing between an upper position and a lower position in the direction of movement of said obturator shaft.

46. The trocar of claim 45 wherein said trocar depression spring is loaded when said shaft is in its retracted position, and said retraction spring is loaded when said retraction assembly is moved to its said lower position by said shaft.

* * * * *